United States Patent [19]

Labbé et al.

[11] Patent Number: 5,021,452
[45] Date of Patent: Jun. 4, 1991

[54] PROCESS FOR ENHANCING WOUND HEALING

[75] Inventors: Robert F. Labbé; Rebecca L. Rettmer, both of Seattle, Wash.

[73] Assignee: The Board of Regents of the University of Washington, Seattle, Wash.

[21] Appl. No.: 501,434

[22] Filed: Mar. 28, 1990

Related U.S. Application Data

[63] Continuation of Ser. No. 295,113, Jan. 9, 1989, abandoned.

[51] Int. Cl.$^5$ .................. A01N 43/08; A61K 31/375
[52] U.S. Cl. .................................. 514/474; 514/844; 514/887; 514/904; 514/912; 204/157.67
[58] Field of Search ........................................ 514/474

[56] References Cited

PUBLICATIONS

Martindale, "The Extra Pharmacopoeia", 28th ed (1982) pp. 1653–1656.

Primary Examiner—Shep K. Rose
Assistant Examiner—T. J. Criares
Attorney, Agent, or Firm—Seed and Berry

[57] ABSTRACT

There is disclosed a process for improving wound healing, comprising administering ascorbate or derivatives thereof to a wound site at a concentration of at least 20 $\mu$mol/L and irradiating the wound site with a low-power laser at a wave length of about 600 nm to about 1100 nm. The process for improving wound healing can be used for the healing of deep, interior wounds with longer wave length radiation and higher energy output radiation. The process can further be used for improving the healing of superficial skin wounds with shorter wave lengths and lower energy output of the low-power laser.

13 Claims, 2 Drawing Sheets

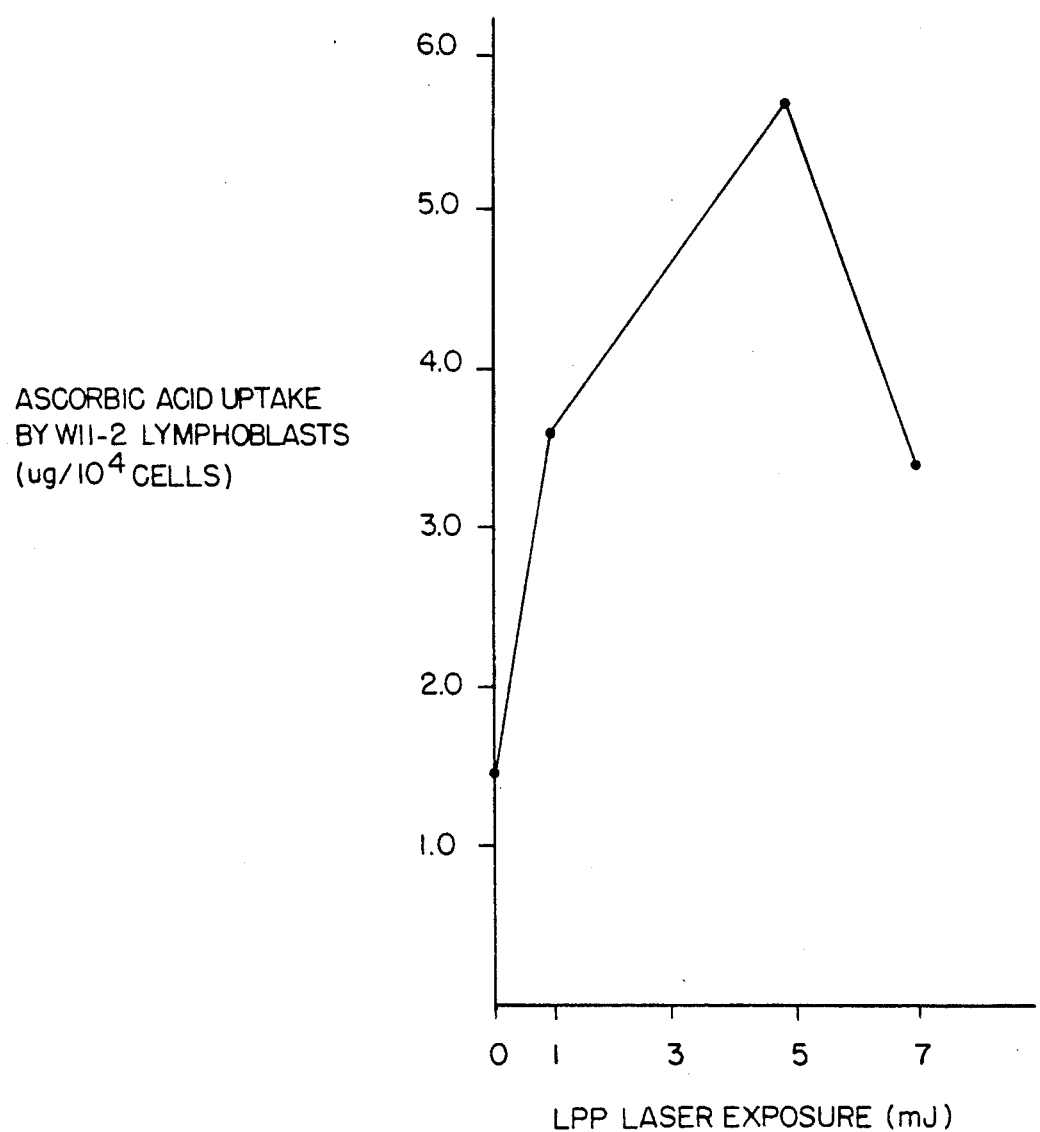

PROCESS FOR ENHANCING WOUND HEALING

CROSS-REFERENCE TO RELATED APPLICATION

This application is a continuation of U.S. application Ser. No. 07/295,113 filed Jan. 9, 1989, now abandoned.

TECHNICAL FIELD

The present invention relates to the synergistic combination of low-power laser irradiation and exogenous ascorbate, ascorbic acid, or derivatives thereof, administration to promote wound healing of either surface or deep, internal wounds.

BACKGROUND OF THE INVENTION

The medical and economic benefits to be gained from improved or enhanced wound healing therapies are obvious. Hence, new methods and processes for promoting wound healing have been continuously pursued, especially for chronic, indolent wounds, which can be a frustrating aspect of patient care.

While high-powered lasers have been accepted and used successfully in a variety of clinical settings, only rarely have low-power lasers been used or even investigated. The clinical applications of low-power continuous wave or pulsed emission lasers operating in the mW range may be potentially extensive. The low-power laser may be especially effective in treating superficial wounds and musculoskeletal disease or injury. Basford, "Low-Energy Laser Treatment of Pain and Wounds: Hype, Hope or Hokum?" *Mayo Clin. Proc.* 61:671-75, 1986, in an editorial critique, reported that "although the substantiation of results has varied greatly in detail and quality, many investigators have described successful treatment of a wide variety of painful musculoskeletal, rheumatologic, and neurologic conditions with low-energy lasers." Such effects of low-power or low-energy lasers are referred to as biostimulation.

Some studies of wound healing have found a "systemic effect" from laser treatment. Pain and inflammation have decreased and healing has improved at sites distant from the treated areas. These observations may be supported by a report of increased excretion of urinary 5-hydroxyindoleacetic acid, a product of serotonin metabolism and the finding of decreased platelet aggregation after laser treatment.

There have been a variety of reported cellular effects following low-energy laser irradiation. These include stimulated collagen production and fibroblast activity, altered prostaglandin content, increased tissue activities of succinic dehydrogenase and lactic acid dehydrogenase, altered rates of DNA synthesis, cytoplasmic changes, and accelerated cellular proliferation.

In human studies, evaluations of wound healing in response to low-power laser treatment have found remarkable results for the healing of cervical erosions and a variety of skin ulcers. The studies, however, tend to be uncontrolled or incompletely described. In addition, other experiments that have involved swine with skin wounds have shown no benefit from laser treatment. Basford states: "It is important to remember that the literature on low-energy laser studies is uneven and disorganized. Future work may show that results now in apparent conflict are actually different aspects of the same problem."

Abergel et al., "Biostimulation of Wound Healing by Lasers: Experimental Approaches in Animal Models and in Fibroblast Cultures," *Dermatol. Suro. Oncol.* 13:1127-33, 1987, refer to a mechanism of action for collagen accumulation as a result of laser treatment. More specifically, Abergel et al. refer to the He-Ne laser as providing irradiation that might increase collagen production by fibroblasts via an enhancement of collagen gene expression on the transcriptional level. Enhancement of collagen accumulation could result from an elevation of collagen mRNA steady-state levels through an activation of the regulatory sequences of the corresponding genes.

A review of laser biostimulation (Enweneka, "Laser Biostimulation of Healing Wounds: Specific Effects and Mechanisms of Action," *J. Orthopaedic Sports Phys and Therapy* 9:333-38, 1988) refers to several proposed mechanisms of action, including suggestions that lasers:

1. Accelerate the inflammatory phase of wound healing by altering the levels of various prostaglandins,
2. Increase ATP synthesis by enhancing electron transfer in the inner membrane of mitochondria,
3. Accelerate protein (collagen) synthesis by accelerating DNA and RNA synthesis,
4. Augment fibroplasia by a mechanism that is still being explored, and
5. Enhance the ability of immune cells to combat invading pathogens.

Accordingly, it is known that low-power lasers have effects on wound healing, but it is still unclear as to the precise mechanism of action of the effects and how best to utilize laser irradiation to enhance or improve wound healing.

In separate and unrelated studies, it has been found that ascorbate is important in the regulation of collagen biosynthesis. The importance of ascorbic acid in the metabolism of connective tissues was realized as early as the sixteenth century. The explorer Jacques Cartier recognized that dietary intake, particularly of citrus fruits, was essential in preventing scurvy and treating those suffering from the disease.

Later studies showed the marked growth of embryonic chick bones grown in tissue culture media supplemented with ascorbic acid when compared to similar bones grown in media without ascorbic acid.

It later became known that ascorbic acid was an essential cofactor in the hydroxylation of proline and lysine to form hydroxyproline and hydroxylysine, amino acids essential to the formation of stable collagen. Hydroxyproline is necessary for collagen helix formation, and in its absence, collagen is unable to be properly secreted from fibroblasts Hydroxylysine is essential in collagen cross-link formation, and in its absence, the collagen would be structurally unstable.

Pinnell, "Regulation of Collagen Biosynthesis by Ascorbic Acid: A Review," *Yale J. Biol. Med.* 58:553-59, 1985, further demonstrated that ascorbic acid is a "fundamental signal for collagen production" which appears to be independent of its cofactor function for hydroxylation of proline and lysine.

Accordingly, it appears as though both low-power laser irradiation and exogenous administration of ascorbic acid can enhance wound healing by independent means. That is, the mechanisms of actions of both forms of wound healing treatment are independent of each other. Accordingly, there is a need in the art to determine the interrelationships of collagen synthesis and wound healing effects of low-power lasers and ascorbic acid. Furthermore, it is not known whether or not each mechanism of treatment of wound healing is acting independently, or if there is an interdependency that can lead to a synergistic combination.

SUMMARY OF THE INVENTION

The present invention is directed to a process for enhancing wound healing, comprising administering ascorbate or ascorbic acid or derivatives thereof to the wound site at a concentration of at least 20 µmol/L and radiating the wound site with a low-power laser at a wave length of about 600 nm to about 1100 nm. The source of the ascorbate, ascorbic acid or derivatives thereof is exogenous administration by standard pharmacological procedures. The ascorbate, ascorbic acid or derivatives thereof may be administered topically directly to the wound site and the surrounding tissue. If the ascorbate, ascorbic acid or derivatives thereof are applied topically, the wound site concentration is at least about 100 µmol/L. Preferably, the concentration range at the wound site with topical administration is from about 100 µmol/L to about 5000 µmol/L. Most preferably, the concentration range is from about 1000 µmol/L to about 4000 µmol/L.

The inventive process can also include the simultaneous or sequential administration of nutrients, such as amino acids, trace elements and vitamins. Preferably, the nutrients are selected from the group consisting of proline, lysine, protein hydrolysate, zinc, calcium, pyridoxin and combinations thereof. Most preferably the concentration of proline is from about 90 µmol/L to about 300 µmol/L and the concentration of lysine is from about 100 µmol/L to about 250 µmol/L.

The laser can either be a pulsed or a continuous wave with the quantity of energy output from about 1.0 mJoule/cm$^2$ to about 1000 mJoules/cm$^2$.

The longer wave lengths and higher energy are required for greater laser penetration for deeper wounds.

The synergistic effect of the inventive process is to greatly increase the cellular uptake of ascorbate in response to the laser irradiation.

BRIEF DESCRIPTION OF THE DRAWINGS

FIG. 2 shows ascorbic acid uptake by WIL-2 lymphoblasts in terms of micrograms per $10^4$ cells as a function of low-power laser irradiation exposure.

DETAILED DESCRIPTION OF THE INVENTION

Figure 1:
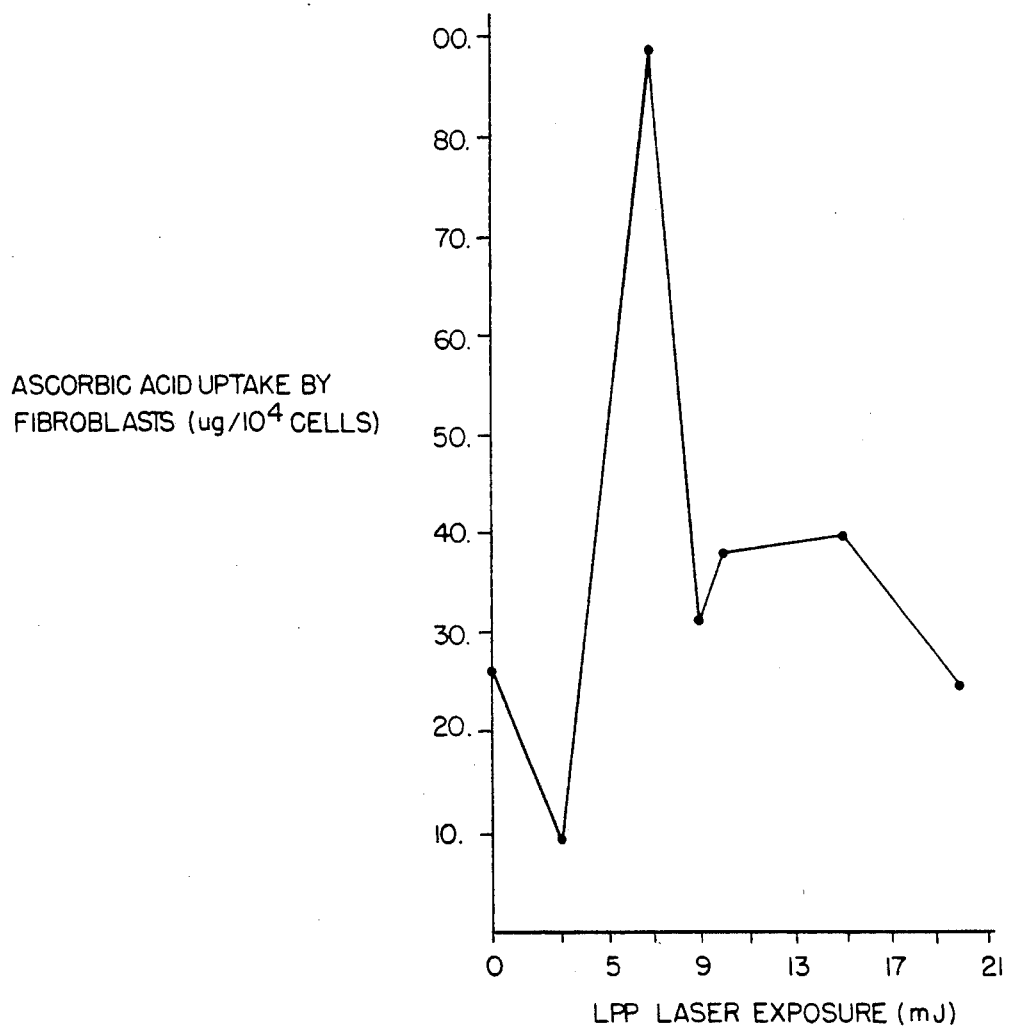
FIG. 1 is a graph showing the ascorbic acid uptake by fibroblasts in terms of micrograms per $10^4$ cells as a function of low-power laser irradiation exposure in terms of milliJoules (mJoules).

The inventive process for improving or enhancing wound healing over the normal physiologic process comprises administering ascorbate or derivatives thereof to the wound site at a concentration of at least 20 µmol/L and irradiating the wound site with a low-power laser at a wave length of about 600 nm to about 1100 nm. The inventive process can further be enhanced with the simultaneous or subsequent administration of nutrients, such as amino acids, trace elements and vitamins to the wound site. Preferred amino acids are proline and lysine. Preferred trace elements are zinc and calcium. Preferred vitamins are ascorbic acid derivatives. Ascorbate derivatives include vitamin C palmitate and other medium to long chain alkyl derivatives ($C_{12}$–$C_{22}$), dehydroascorbic acid and other biologically active derivatives. The ascorbate derivative concentration is at least 85 µmol/L. Preferably, the ascorbate derivative concentration is at least 180 µmol/L.

Ascorbate is commonly administered as the free acid, ascorbic acid. Ascorbic acid is readily absorbed from the gastrointestinal tract after oral administration. Other forms of administration for ascorbate or derivatives thereof include intravenous, subcutaneous, intramuscular, intralymphatic, intranasal, intrathecal, intraperatoneal, and by injection or topical application directly into the wound site and/or the surrounding tissue.

It is necessary that the concentration of ascorbate or derivatives thereof surrounding or bathing the wound site be at least 20 µmol/L. Preferably, the concentration of ascorbate or derivatives thereof is at least 80 µmol/L. After oral or systemic administration of ascorbic acid it is possible to achieve serum concentrations as high as 142 µmol/L with normal kidney function. However, higher serum concentrations can rarely be achieved because the kidney reabsorption mechanism cannot maintain serum concentrations in excess of 142 µmol/L. However, if kidney function is compromised, higher concentrations (lower in dialysis patients) can be achieved. Therefore, higher wound site concentrations can only be achieved by direct injection or topical application to the wound site and/or surrounding tissue.

The lasers used for the inventive process have a low-energy output and a wave length from about 600 nm to about 1100 nm. The energy output of the laser can be in either a pulsed or a continuous mode. This translates to an energy delivery from about 1.0 mJoules/cm$^2$ to about 1000 mJoules/cm$^2$. For superficial wounds, such as skin wounds, the low-power laser having shorter wave lengths of from about 600 nm to about 900 nm and the lower energy outputs of from about 1.0 mJoules/cm$^2$ to about 100 mJoules/cm$^2$ is used.

For deeper, interior wounds the low-power laser irradiation should have a longer wave length of from about 900 nm to about 1100 nm and energy delivery of from about 1.0 mJoules/cm$^2$ to about 1000 mJoules/cm$^2$.

Research with the human fibroblast culture system (ATCC #CRL-1471) has been established for studying biostimulation by the low-power laser. Laser irradiation of the fibroblast culture under optimized growth conditions does not alter cell viability, rate of cell proliferation, gross cellular morphology, mitotic index, or DNA synthesis. It was determined that varying levels and types of energy input into the cultured fibroblasts altered the stimulation of hydroxyproline determined that varying levels and types of energy input into the cultured fibroblasts altered the stimulation of hydroxyproline synthesis, a collagen precursor. Moreover, hydroxyproline formation can be accelerated several-fold in the presence of added proline, indicating that this substrate becomes limiting quickly in the basic culture system and in vivo.

It was found that fibroblasts in culture are stimulated to concentrate intracellular ascorbic acid from an exogenous source by low-power laser irradiation.

The following examples are intended for illustrative purposes and not to limit the scope of the invention.

EXAMPLES

EXAMPLE 1

A Ga-Al-As low-power pulsed (LPP) laser was constructed by BGR, Fife, Wash., with facility for varying both pulse width and pulse repetition rates. The nominal wave length emitted is 904 nm. The peak power output is 2 W; average power is in the mW range. A monitoring circuit was incorporated for confirming energy output. Energy output was proportional to pulse width at constant pulse frequency. The probe tip was adjusted so that the beam covered approximately 1.0 cm$^2$ at the cell layer. The laser output was calibrated with a Model 88XLA Radiometer/Photometer (Photodyme, Inc., Newbury Park, Calif.) and the beam pattern or exposure field was determined using infrared sensor cards (Quantex, Rockville, Md.). The energy transmittance of the culture media and incubation containers were also measured. In this way, it was determined that transmission attenuation did not pose a problem with attaining reproducible incident radiant energy on the cells.

EXAMPLE 2

Growing lymphoblasts were irradiated twice daily on days three, four and five during the log phase of growth. The exposure level of irradiation for each time interval (i.e., six exposures total for each cell culture) are shown on the X-axis in FIG. 1. After the fifth exposure, the growth media were replaced with a phosphate buffer saline (PBS) solution containing 4000 μmol/L ascorbic acid. Following a further 20 minute incubation at 37° C., the intracellular uptake of ascorbic acid was determined. The results of the intracellular uptake of ascorbic acid per 10$^4$ cells is shown in FIG. 1.

EXAMPLE 3

Growing fibroblasts were irradiated twice a day on days three, four and five during the log phase of growth using WII-2 lymphoblasts grown in suspension culture. After the day five irradiation exposure, ascorbic acid at a concentration of 4000 μmol/L was added directly to the growth media. Following a further 20- minute incubation, the intracellular content of ascorbic acid was assayed and the results are shown in FIG. 2. The results of Examples 2 and 3 show that essentially the same irradiation parameters that optimized ascorbate uptake into fibroblasts had a similar effect on cultured lymphoblasts.

We claim:

1. A process for enhancing cellular uptake of ascorbate, ascorbic acid or dehydroascorbic acid at a wound site of a mammal, comprising administering to the wound site ascorbate, ascorbic acid or dehydroascorbic acid at an extracellular concentration measured at the wound site of at least 20μmol/L and also irradiating the wound site with a low-power laser at a wave length of from about 600 nm to about 1100 nm.

2. The process of claim 1, further comprising administering a therapeutically effective amount of a nutrient or nutrients to the wound site, wherein the nutrient or nutrients do not contain ascorbate, ascorbic acid or dehydroascorbic acid.

3. A process for enhancing cellular uptake of ascorbate, ascorbic acid or dehydroascorbic acid at an interior wound site of a mammal comprising internally administering ascorbate, ascorbic acid or dehydroascorbic acid to increase the concentration of circulating ascorbate, ascorbic acid or dehydroascorbic acid to an extracellular concentration at the wound site of at least 20μmol/L and also externally irradiating the wound site with a low-power laser at a wave length of from about 600 nm to about 1100 nm and energy delivery from about 1.0 mJoules/cm$^2$ to about 1000 mJoules/cm$^2$.

4. The process of claim 3, further comprising administering a therapeutically effective amount of a nutrient or nutrients to the wound site, wherein the nutrient or nutrients do not contain ascorbate, ascorbic acid or dehydroascorbic acid.

5. The process of claim 3 wherein the extracellular concentration of ascorbate, ascorbic acid or dehydroascorbic acid at the wound site after oral or systemic administration is from about 20μmol/L to about 142μmol/L.

6. A process for enhancing cellular uptake of ascorbate, ascorbic acid or dehydroascorbic acid at a surface wound site of a mammal, comprising administering directly to the wound site ascorbate, ascorbic acid or dehydroascorbic acid to increase the extracellular concentration measured at the wound site to at least 20μmol/L and also irradiating the wound site with a low-power laser at a wave length from about 600 nm to about 1100 nm and an energy delivery from about 1.0 mJoules/cm$^2$ to about 1000 mJoules/cm$^2$.

7. The process of claim 6, further comprising administering a therapeutically effective amount of a nutrient or nutrients to the wound site, wherein the nutrient or nutrients do not contain ascorbate, ascorbic acid or dehydroascorbic acid.

8. The process of claim 7 wherein the nutrient is an amino acid, a trace element, a vitamin, or a combination thereof.

9. The process of claim 7 wherein the nutrient or nutrients are selected from the group consisting of proline, lysine, protein hydrolysate, zinc, calcium, pyridoxin and combinations thereof.

10. The process of claim 9 wherein the nutrient is proline or lysine.

11. The process of claim 10 wherein the extracellular proline concentration measured at the wound site is from about 90μmol/L to about 300μmol/L and the extracellular lysine concentration measured at the wound site is from about 100μmol/L to about 250μmol/L.

12. The process of claim 6 wherein the laser has an energy output in either pulsed or continuous mode.

13. The process of claim 6 wherein the extracellular concentration of ascorbate, ascorbic acid or dehydroascorbic acid at the wound site after direct injection or topical application to the wound site is from about 100μmol/L to about 5000 μmol/L.

* * * * *

UNITED STATES PATENT AND TRADEMARK OFFICE
CERTIFICATE OF CORRECTION

PATENT NO. : 5,021,452

DATED : June 4, 1991

INVENTOR(S) : Robert F. Labbé; Rebecca L. Rettmer

It is certified that error appears in the above-identified patent and that said Letters Patent is hereby corrected as shown below:

Column 1, line 3, insert the following:
--This invention was made with government support under grant number 1R03 RR02572 awarded by the National Institutes of Health. The government has certain rights in this invention.--.

Signed and Sealed this

Sixth Day of July, 1993

*Attest:*

MICHAEL K. KIRK

*Attesting Officer*  Acting Commissioner of Patents and Trademarks